(12) United States Patent
Shoenfeld (10) Patent No.: US 8,473,097 B2
(45) Date of Patent: *Jun. 25, 2013

(54) PASS-THROUGH WALL-MOUNTED MEDICATIONS CABINET WITH UV STERILIZATION

(75) Inventor: Norman A. Shoenfeld, Livingston, NJ (US)

(73) Assignee: S & S X-Ray Products, Inc, Den Argyl, PA (US)

( * ) Notice: Subject to any disclaimer, the term of this patent is extended or adjusted under 35 U.S.C. 154(b) by 207 days.

This patent is subject to a terminal disclaimer.

(21) Appl. No.: 13/188,102

(22) Filed: Jul. 21, 2011

(65) Prior Publication Data

US 2012/0153783 A1 Jun. 21, 2012

Related U.S. Application Data

(63) Continuation-in-part of application No. 12/968,340, filed on Dec. 15, 2010, now Pat. No. 8,160,741.

(51) Int. Cl.
*G06F 17/00* (2006.01)

(52) U.S. Cl.
USPC .............................. 700/237; 221/92; 221/282

(58) Field of Classification Search
USPC ..................... 700/237; 221/282, 92; 312/209, 312/4
See application file for complete search history.

(56) References Cited

U.S. PATENT DOCUMENTS

| | | | | |
|---|---|---|---|---|
| 5,160,699 | A * | 11/1992 | Siegal | 422/24 |
| 6,079,216 | A * | 6/2000 | de Marsillac Plunkett et al. | 62/56 |
| 6,171,548 | B1 * | 1/2001 | Rose et al. | 422/20 |
| 7,604,012 | B2 * | 10/2009 | Alpert et al. | 134/58 D |
| 8,160,741 | B1 * | 4/2012 | Shoenfeld | 700/237 |
| 2003/0034459 | A1 * | 2/2003 | Bonin | 250/491.1 |
| 2007/0202005 | A1 * | 8/2007 | Maschke | 422/3 |

* cited by examiner

*Primary Examiner* — Timothy Waggoner
(74) *Attorney, Agent, or Firm* — Bernhard P. Molldrem, Jr.

(57) ABSTRACT

A self-sterilizing pass-through medications cabinet is built into a wall of a hospital room and can be accessed from the room interior or from the hallway. A frame mounted in the wall supports a rack or box containing patient drawers or bins, arranged in a vertical stack parallel to the wall or in a horizontal row. A hall-side door can be opened by pharmacy staff to place pre-loaded bins into respective compartments, and one or more room-side doors or drawers are opened by nurse staff for administering the medications to patients. The hallway door and room doors interlock to prevent their being opened at the same time to safeguard patient privacy. An ultraviolet germicidal illumination system bathes each bin in sterilizing radiation to destroy pathogens that may be present from handling or transport of the bins.

19 Claims, 11 Drawing Sheets

PASS-THROUGH WALL-MOUNTED MEDICATIONS CABINET WITH UV STERILIZATION

This is a Continuation-in-Part of my U.S. patent application Ser. No. 12/968,340, filed Dec. 15, 2010 now U.S. Pat. No. 8,160,741.

BACKGROUND OF THE INVENTION

This invention relates to cabinets or storage facilities for keeping patient medications and prescription drugs for a given patient. The invention is more specifically directed to a locking, self-sanitizing cabinet suitable for use in a hospital or health care facility, mounted in or on the wall of a patient room in a hospital or health care facility, to secure pharmaceuticals for a given patient or group of patients, to avoid hospital-acquired infections, and to facilitate keeping an audit trail of access to the items stored in the cabinet.

In general, pharmaceuticals are delivered to patients when needed, and this typically involves use of a medications cart containing the prescription medications for the patients on a given floor of the hospital or health center. The cart is typically loaded in a pharmacy department and then is brought to the particular hospital floor. The cart is wheeled from room to room to deliver each patient his or her drugs at the time that the nurse or other practitioner is to administer them. The use of a cart has been more convenient and more efficient than obtaining each patient's medications individually. However, the use of a cart to transport medications room to room is inefficient and awkward. The medications cart takes up valuable space in the hallway and corridors. Administering drugs from the cart involves bending and stooping to obtain the drugs from lower drawers. If the nurse needs a particular drug for one of her patients when another nurse has the cart for her medication rounds, then the first nurse has to spend time hunting the cart down and often it is difficult to find the cart. Also, when the pharmacy staff comes to the floor to restock the cart, the cart is often in use and difficult to find, resulting in wasted time for the pharmacy staff. Often, the cart does not fit into the patient's room. In addition, the portable cart requires periodic charging of its batteries, and this task is often overlooked and forgotten until a failure occurs. Also, when a patient's bed or other large equipment item needs to be urgently moved into the hallway, any medication carts that are plugged into wall outlets to recharge can present a significant obstruction.

It is more convenient and better use of the nurse's time and efforts to keep the pharmaceuticals at the patient locations, i.e., in the patient's room or ward, or in the cluster of rooms where the patient is located. Medications need to be secured at the place of administration, that is, kept locked with a key lock or other mechanism, with access limited only to persons in the nursing staff and pharmacy staff. A record of access to the pharmaceuticals needs to be maintained, but this usually requires making pen-and-ink entries on a paper record, or separately keying in information on separate computer work station.

My earlier U.S. Pat. No. 7,668,620 discloses a wall-mounted pharmacy cabinet situated at the patient location. Medications prescribed for a patient can be loaded into the cabinet by pharmacy staff and stored securely until administered to the patient. The system automatically tracks access to the cabinet. Nurse staff can access the cabinet electronically (e.g., using a pass-code, a barcode reader, RFID device, fingerprint scanner or wireless means). The medications cabinet is kept secure, and with its drawers being closed and locked after each use.

It is desired for the pharmacy staff to be able to load these wall-mounted cabinets from the hallway, without having to actually enter the patient room. It is also desirable to protect patient privacy. All the advantages of the wall-mounted pharmaceutical cabinet (U.S. Pat. No. 7,668,620) should also be present in any improved cabinet as well. Where multiple patients occupy a hospital room, each patient should be provided with a respective drawer or bin, with the nurse being able to access these bins individually. At the same time, the pharmacy staff should be able to load all the bins or drawers for a given cabinet at one time. Alternatively, bins can be assigned specifically for different users, and for different functions. For instance, a bin can be assigned to be accessed only by respiratory therapy, and a bin can be assigned to store the patient's medication brought to the hospital from home, a bin can be used for secure storage of patient's belongings, and controlled substances can potentially be stored by incorporating a secondarily locked compartment within the cabinet.

As a means for reducing the incidence of hospital-acquired infections, it would be advantageous for the bins, as well as the medications and other items stored in the bins, to be sanitized and/or sterilized to destroy any bacteria, virus or other pathogens that may be present from handling or transportation of the bins. The passthrough cabinet also reduces traffic into and out of the patient's room, thereby reducing the chances to spread infection both into the patient's room and from the patient's room to other hospitalized patients.

OBJECTS AND SUMMARY OF THE INVENTION

Accordingly, it is an object of the present invention to provide a secure medications cabinet that avoids the drawbacks of the prior art.

It is another object to provide a medications cabinet and tracks of the identity or persons accessing the cabinet and times of such access, for each drawer or bin of the medications cabinet.

More particularly, it is an object to provide an in-wall pass-through medications cabinet to be accessed by pharmacy staff from the hallway side and accessed by nursing staff from the room side, with a number of individually locking bins or bins within locking compartments.

It is a related object that the drawers or compartments can be individually accessed by the nurse, one at a time, and pharmacy access is available by means of a single access door outside the room.

A further object is that access should be possible from only one side at a time, so as to maintain privacy, but that the bins or drawers can be removed and replaced from either side.

Another important aspect of this invention is to achieve sterilization of the bins or drawers, as well as any medication containers being stored there, after the bins have been transported to the storage cabinet, but before the nurse or other practitioner administers the medications to the patient, to reduce the potential to spread infection.

According to an aspect of the present invention, a pass-through medications cabinet is built into a hospital wall, i.e, mounted in a wall of a patient room, where the wall separates the patient room from a hallway that passes along a number of hospital rooms. An enclosure frame is mounted into the wall and is disposed at an elevated position above the floor of the patient room, so that there is a room side that may be opened to the patient room and a hallway side that may be opened to the hallway. Within the frame there are a number of horizontal support racks or compartments, with elongated medication bins disposed on respective ones of the racks. The racks or compartments and their associated bins are arranged in a row or in a vertical stack (in a preferred embodiment), one above another and each being oriented laterally in the cabinet frame. That is, the racks and associated bins extend parallel to the wall. In an alternative embodiment, the bins or drawers can be in a horizontal row, at a right angle to the wall. A first, hallway-side door is located on the hallway side of the cabinet and is hinged onto the enclosure frame of the cabinet. This door can be opened in the hallway to provide pharmacy personnel with access all of the racks from the hallway side of the cabinet. From this side the pharmacy staff can restock the medications cabinet without having to enter the patient room, with each door corresponding to a particular compartment and bin. The hall door can incorporate a smoke-proof design and self-closing feature. A number of second, patient-side or room-side doors are located on the room side of the cabinet. Each of these doors is positioned in front of a respective one of the racks. The second doors can each be opened individually to access the patient medication bin in the respective rack. A controllable door lock arrangement is associated with the first, hallway-side door and said second, room-side doors. This permits the first, hallway-side door to be opened only when all of the second, room-side doors are closed, and permits the second doors to be opened only when the first, hallway-side door is closed. In a preferred embodiment, the room-side doors are also interlocked so that they can be opened only one door at a time, i.e., to administer medications to a specific patient in the room. Favorably, this can include a bin sensor in the compartment as an option, so that the bin would need to be reinserted into the compartment and the door closed before the nurse can access another compartment.

The controllable door lock mechanism can take the form of an electronic latch for the first door, and may be actuable by a specific pharmacy staff key device. The second door latch mechanism, which unlocks one or more of the room-side second doors, may be actuable by a second device specific to the nurse staff. This may employ RFID technology or bar code technology, for example, or may require entering an identity and/or code into a computer or touch screen. The pharmacy staff access may also occur by means of a physical key lock.

The pass-through cabinet of this invention can also be configured with mechanical door locks and mechanical interlocks, but with the UVGI feature for each of the drawers or bins in the cabinet, and which would be energized on for a sufficient time for sterilizing the interior of the cabinet when the doors are closed and locked.

The preferred configuration incorporates an IP-addressable cabinet. The pharmacy technician can log into the system once with a password and an ID, using software on a mobile PC, i.e., a tablet PC, and then can select and open cabinets throughout a nursing unit without having to re-enter logic information for every cabinet.

Favorably, the enclosure frame of the cabinet is substantially flush with the wall surface on the hallway side, so that the cabinet does not project into the hallway.

The passthrough cabinet can have an internal locking compartment to store narcotics or other controlled substances. These can be additionally security-protected by a second internal locking system.

In self-sterilizing or self-sanitizing embodiments of the cabinet, there are one or more ultraviolet germicidal illuminator or UVGI devices situated on a surface of the rack above each respective bin or drawer. The UVGI devices are controllably actuated so as to bathe the bin and its contents in short wavelength ultraviolet light to destroy bacteria and virus (or fungal spores or other pathogens) that may be present. When either the hall side door or room-side door(s) are closed after depositing or accessing the bin(s), the ultraviolet light generators are turned on for a prescribed period of time, and then automatically turn off. When the ultraviolet lights are on during a sterilization cycle, either opening a door will turn the UV lights off until the door is again closed, or else the door interlock mechanism will prevent access, such that the doors are not permitted to open until the sterilization cycle (typically, a few minutes) is complete.

For destruction of microorganisms for the purpose of decontamination of the surfaces of the bins and medication containers, the UV wavelengths should be in the range of about 240 nm to 280 nm, and favorably about 265 nm. This can be achieved with various UV discharge lamps, or with UV LED devices. The solid state devices can be fabricated with a band gap energy of about 4.68 eV, and formed of a GaN or GaAlN material.

In another embodiment, the medication cabinet adapted to be mounted on a wall of a patient room and is loaded and accessed from within the patient room. In this embodiment the cabinet enclosure has a front wall and at least one side wall, with one or more locking drawers in the enclosure. Each drawer includes a medications bin having a proximal end disposed, when the bin is in its closed position, at the side wall, and a distal end situated within the enclosure. A slide means permits the bin to be pulled out to an open position to allow access to the bin and to be pushed back in to its closed position. A releasable latch feature within the enclosure releasably engages a member on the respective bin in its closed position to lock the drawer, and can be moved between a locked position and an unlocked position in which the latch feature releases that member. An ultraviolet germicidal illuminator device is disposed above the respective medication bin in each drawer. An automatic access feature permits an authorized person to actuate the releasable latch means to its unlocked condition to permit access to the drawer and automatically returns the latch feature to its locked position to secure the drawer bin when returned to its closed position. The cabinet also includes a sterilization control feature that is associated with the automatic access and with the ultraviolet germicidal illuminator devices, and is sensitive to the closing of said drawers. This feature energizes the ultraviolet germicidal illuminator devices ON for a predetermined time when said bins have been inserted into said drawers and pushed in to their closed positions. This may included the interlock feature that is employed in the other embodiments, to prevent the drawers from being unlocked when the ultraviolet germicidal illuminator devices have been energized ON until the predetermined sterilization time has elapsed.

The following chart explains the dosage of UV radiation required to kill several specific microorganisms that have been identified as pathogens Germicidal Ultraviolet Dosage

| 1. Pathogenic Microbe | Abbreviated nomenclature | Type of disease | | Dosage* |
|---|---|---|---|---|
| Corynebacterium diphtheriae | C. diphtheriae | Bacteria | Diptheria | 6,500 |
| Legionella pneumophila | L. pneumophila | Bacteria | Legionnaire's Disease | 2,700 |

-continued

| 1. Pathogenic Microbe | Abbreviated nomenclature | Type of disease | | Dosage* |
|---|---|---|---|---|
| Mycobacterium tuberculosis | M. tuberculosis | Bacteria | Tuberculosis (TB) | 10,000 |
| Pseudomonas aeruginosa | P. aeruginosa | Bacteria | | 3,900 |
| Serratia Marcescens | S. marcescens | Bacteria | | 6,160 |
| Staphlylococcus aureus | S. aureus | Bacteria | | 6,600 |
| Staphlylococcus epidermidis | S. epidermidis | Bacteria | | 5,800 |
| Adeno Virus Type III | | Virus | | 4,500 |
| Coxsackie A2 | | Virus | | 6,300 |
| Influenza | | Virus | Flu | 3,400 |

(*μW Sec/cm2 for 99% or greater effectiveness against identified pathogen)

According to another favorable embodiment, a pass-through medications cabinet, also adapted to be mounted in a wall of a patient room, i.e., built-in, has an enclosure frame mounted in the wall and disposed at an elevated position above a floor of the room and has a room side that may be opened to the patient room and a hallway side that may be opened to the hallway. A medications cabinet box is mounted to one lateral side of the enclosure frame, which leaves an access space within the remaining lateral side of the enclosure frame. The box holds a number of pull-out medication bins or drawers stacked one above the other in the box. These drawers are disposed laterally to pull out into the access space within the enclosure frame. A first, hallway-side door is located on the hallway side of the cabinet and is hinged onto the enclosure frame. This first door can be unlocked and opened so that a pharmacy technician can reach into the access space within the enclosure frame.

One (or more than one) second or room-side door is located on the room side of the cabinet and is positioned in front of the afore-said access space. This door can be opened from within the patient room to access the pull-out medication drawers.

A controllable door lock mechanism is associated with the first door and second door. That door lock mechanism permits the first door to be opened only when the second door is closed and permits the second door to be opened only when the first door is closed. A controlled access mechanism in the medications box permits medication drawers to be pulled out one at a time only, when accessed from said room side.

Favorably, each of the medication drawers can be pulled out and detached from the medication cabinet box for administering medication to the patient, and can then be re-inserted back into the box and pushed back fully into the box. The drawer or bin can be removed from either the hallway side or the room side.

Preferably, there is a tip-down shelf mounted on the room side or proximal side of the box. This shelf pivots between a raised position, in which the shelf is vertical and substantially flush with a proximal side of the box, and a lowered, horizontal position for supporting the medications drawer when the medications are being administered to the patient. There can be a walled shelf built into the lower portion of the second door and extending transversely across the door. This shelf may be used for storing non-medication materials, e.g., swabs, bandages, alcohol, or similar items.

In favorable embodiments, the medication drawers lie parallel to the wall. Also, in a preferred design, the first or hallway-side door is substantially flush with the surface of the wall on the hallway side. In an alternative embodiment, the drawers or bins may be arranged in a horizontal row, and with all the bins accessible from the hallway side, and each drawer being pulled out one at a time on the room side.

In the medications cabinets of this invention, access to the locked medication storage is available from both inside the room (for the nurse staff) and from the hallway (for the pharmacy staff). This has the great advantage that the pharmacy staff does not enter the patient's room to restock the patient's medications. This makes more efficient use of pharmacy personnel time, helps guard the patient's privacy, and reduces the risk of transmission of disease. The compartments or bins are individually locking and accessible by the care-giving staff only for each respective patient. The hallway side door can be constructed to be fire-proof and smoke-proof, so as to meet general hospital building standards.

The pass-through cabinet can be opened only from one side at a time, which maintains privacy in the patient room, as one cannot see into the patient room when the hallway-side door is opened.

The bins or drawers can be removed from either side, although only one bin or drawer may be taken at a time from the room side.

As with the first embodiment, the cabinet has a plurality of UVGI devices so that each one of the drawers or bins can be bathed with disinfecting ultraviolet radiation after the bins have been loaded into the cabinet. The interlock associated with the cabinet prevents the drawers from being opened during a sterilization cycle, or alternatively the interlock may interrupt the sterilization cycle if the medications from one or another of the drawers are needed to be administered to a patient.

A computer or electronic sensor tracks the opening of the doors or opening of the bin drawers, and helps maintain an audit trail of when each drawer was accessed and by whom. A trusted personnel manual over-ride feature can be included, for access during power outages or other malfunction. Normal locking and access are electronically controlled. A touch-screen panel, membrane switch, or PC control may be used for in-room opening. A touch screen panel, membrane switch, hand-held device, or other electronic key arrangement can be used for pharmacy access via the hallway-side door. The over-ride feature can be used to terminate or interrupt a UV sterilization cycle.

The above and many other objects, features, and advantages of this invention will become apparent from the ensuing description of selected preferred embodiments of this invention, with reference to the accompanying Drawing.

DETAILED DESCRIPTION OF THE PREFERRED EMBODIMENTS

Figure 1:
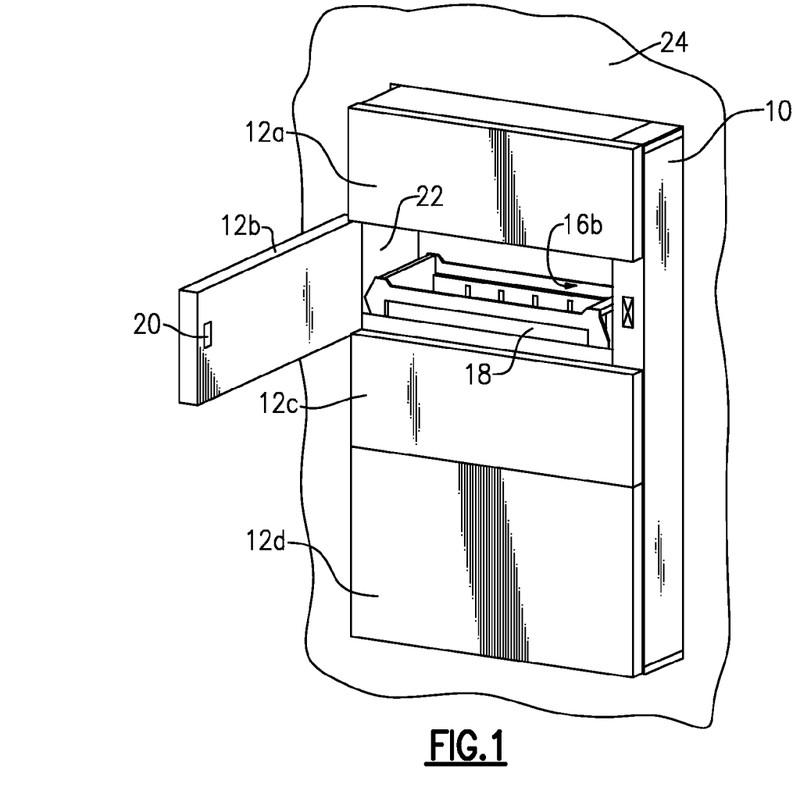
FIG. 1 and FIG. 2 are room-side perspective views of the wall-mounted pass-through dispensing cabinet according to one preferred embodiment, showing one upper compartment open and showing a lowermost compartment open, respectively.
Figure 2:
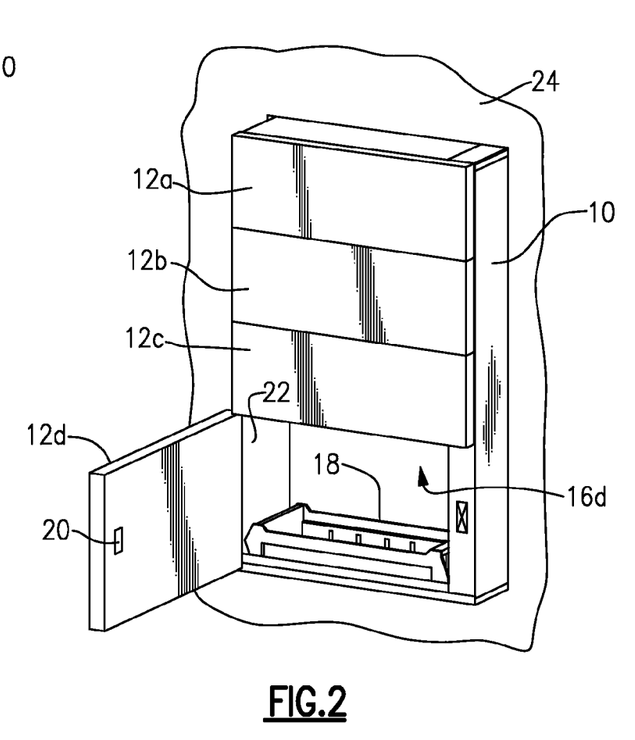
Figure 3:
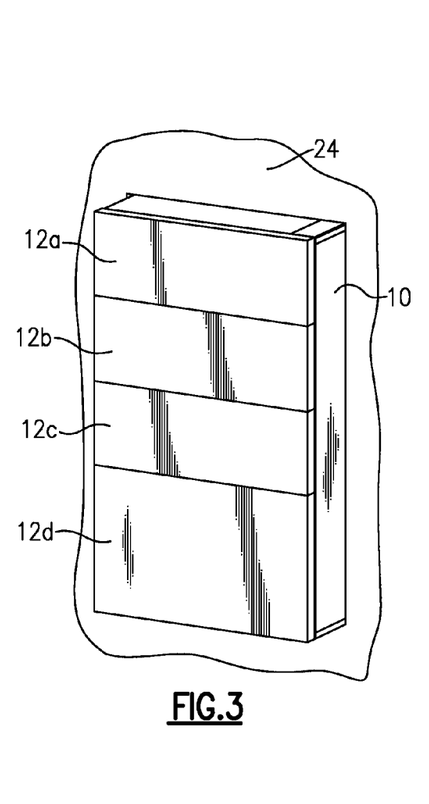
FIG. 3 is a room-side perspective of this embodiment, with all access doors closed.
Figure 4:
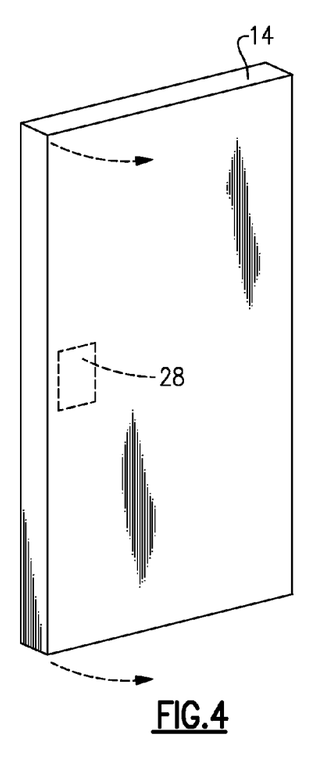
FIG. 4 and FIG. 5 are hallway-side perspective views thereof, with the hallway-side door closed and with the hallway-side door opened, respectively.
Figure 5:
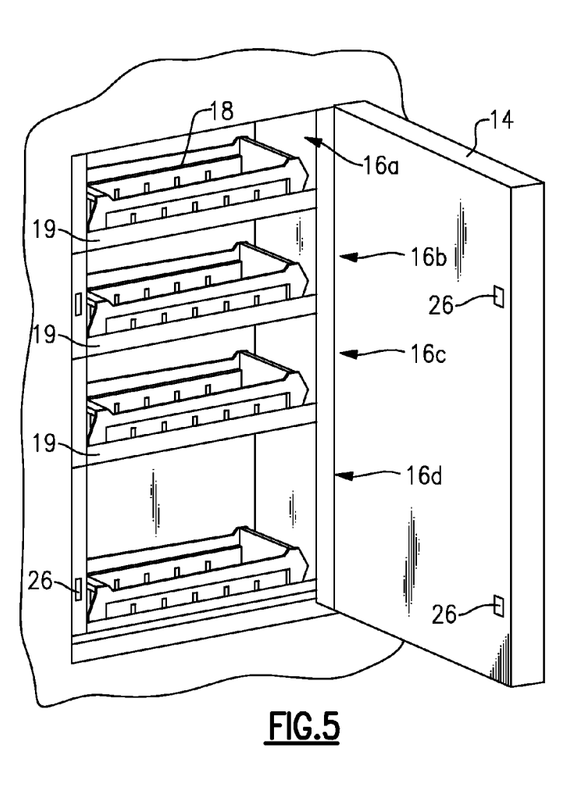

With reference to the Drawing, and initially to FIGS. 1 to 5 thereof, a built-in pass-through medications cabinet 10 is shown from the hospital room side in FIGS. 1, 2, and 3 and is shown from the hallway side in FIGS. 4 and 5. The cabinet has a number of cabinet doors 12a, 12b, 12c, 12d on the room side, and these are stacked one above the other and are hinged to open from the right. On the hallway side there is a single cabinet door 14, which in this embodiment opens from the left. Each of the room-side doors 12a to 12d opens to reveal a respective compartment 16a to 16d, and in each compartment there is an individual medications bin 18. FIG. 1 shows one door 12b of the upper compartments opened, FIG. 2 shows the door 12d for the lowermost compartment open, and FIG. 3 shows the cabinet 10 with all the doors 12a, 12b, 12c and 12d closed. Each compartment has a shelf or rack 19 on which its respective bin 18 is supported. Each door 12a to 12d has a lock 20, which holds the respective door shut and has to be released before the door can be opened. Also, as seen in FIGS. 1 and 2 the cabinet has a frame 22 on which the doors 12a to 12d and 14 are mounted, and defining the right and left ends of the compartments. One component of each door lock 20 is fitted into the frame 22 and another component into the free or non-hinge end of the respective door (12b in FIGS. 1 and 12d in FIG. 2). Here, the frame 22 is mounted into the hospital room wall 24 such that the cabinet projects out from the wall a short distance at location above the floor of the room. As the compartments and bins are oriented transversely, and lie parallel to the wall, the distance that the cabinet projects into the room is kept to a minimum.

The outside, i.e., hallway side or corridor side of the cabinet 10 is seen in FIGS. 4 and 5, with the hallway-side door 14 being shut in FIG. 4 and open in FIG. 5. Here, the door 14 opens to reveal all four of the compartments 16a, 16b, 16c, and 16d, and all four of the respective medications bins 18. A lock mechanism 26 of the hallway-side door 14 is shown partly located in the inside of the free edge of the door 14 and a cooperating portion in the cabinet frame 22. A lock or latch control mechanism 28 is contained in the door 14 and its general position is indicated in dash lines. This can be actuated by pharmacy staff using RFID technology, mag card technology, or from a hand-held device, for example. With this hallway-side door 14 open, all four of the bins 18 can be accessed and changed out in accordance with the pharmacy order for each patient in the respective room. The cabinet(s) can also be accessed through the wired or wireless hospital network, so that the pharmacy technician can enter one passcode to access the system, and then select which of multiple cabinets to open (e.g., the cabinet at the technician's location) and then move onto the next one, etc., and select the next cabinet without having to re-enter his log-on information.

As shown in FIG. 4, one surface of the door 14 is substantially flush with the corridor side of the wall 24, and the cabinet 10 does not project into the hallway or corridor, where space is often limited. In other implementations, the door can be recessed somewhat, so that the door 14 itself does not project into the hallway.

In this embodiment, there is an internal interlock feature whereby only one of the room-side doors 12a, 12b, 12c, and 12d can be opened at any one time, and the nursing staff can access only the one bin 18 for a given patient at a time. The accessed compartment door has to be closed before another compartment door can be opened. In addition, the interlock allows the outer or corridor-side door 14 to be opened only when all of the room-side doors 12a to 12d are shut, and also allows the room-side doors 12a to 12d to be opened only when the corridor-side door 14 is shut. This feature precludes having inside doors and outside door or doors opened at the same time. This feature protects patient privacy, as it makes it impossible to see into the room through the cabinet.

While not shown here, the cabinet 10 may include a tip-down shelf at the room side, of the type described in connection with the next embodiment. The tip-down shelf can serve as a work area for the nursing staff.

Figure 5A:
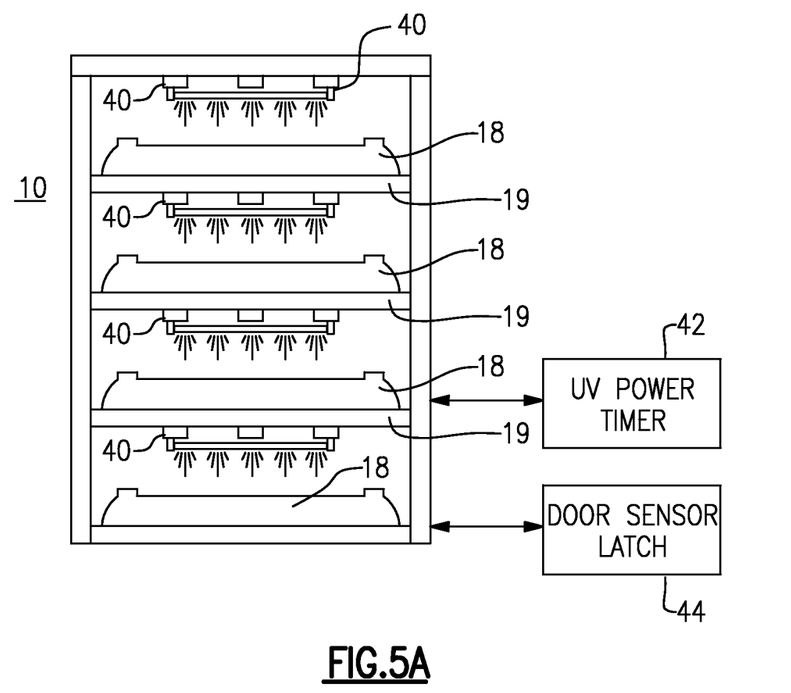
FIG. 5A is a schematic elevational view showing the UVGI feature incorporated into this embodiment.

As shown in FIG. 5A, in this embodiment there is an array of ultraviolet germicidal illuminator (UVGI) devices 40 disposed on the underside of the surfaces of the racks 19 above each of the respective bins 18. These devices 40 can favorably be implemented from UV fluorescent tubes, and there may be one or two tubes extending above each bin or drawer. As an alternative, ultraviolet LEDs, generating UV-C radiation at a wavelength at or near about 265 nm, are another possibility. An associated UV power and timer circuit 42, shown schematically, energizes these devices 40 during a sterilization cycle of a programmed duration. This circuit 42 is coupled to a door sensor and latch control 44, such that the sterilization cycle commences when the control 44 senses that the doors of the cabinet 10 have been closed, and holds the latch mechanisms closed until the sterilization cycle has timed out. The UVGI devices bathe the bins 18 and their contents with sufficient short wavelength UV radiation to destroy any pathogens that may have been picked up by the bins during handling and transport. In other embodiments, other types of UV light sources could be employed, so long as the source of UV light is present above the shelves or bins and the UV radiation is incident on the entire contents of the cabinet, including the bins and their contents.

Figure 6:
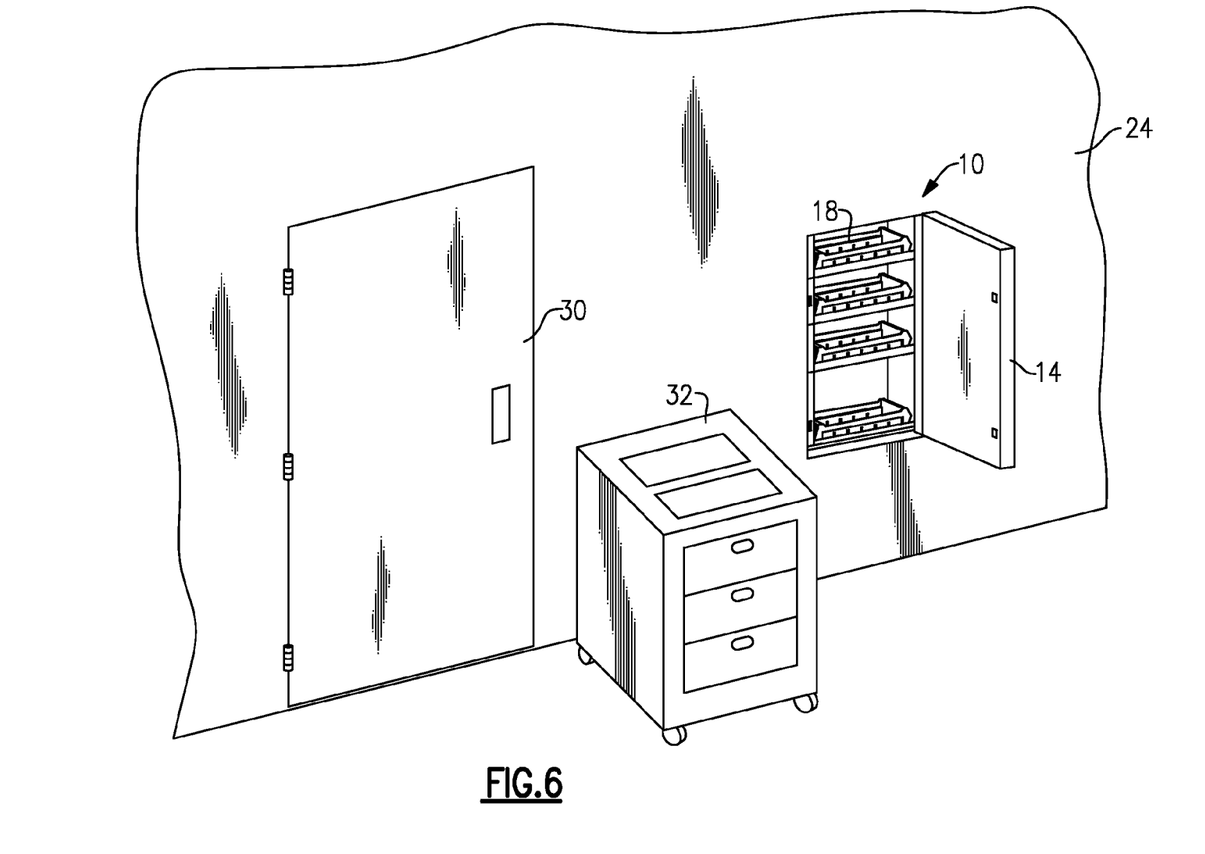
FIG. 6 is an environmental view of a hospital hallway outside a patient's room showing a pharmacy rolling cart and the pass-through dispensing cabinet of this embodiment.
Figure 7:
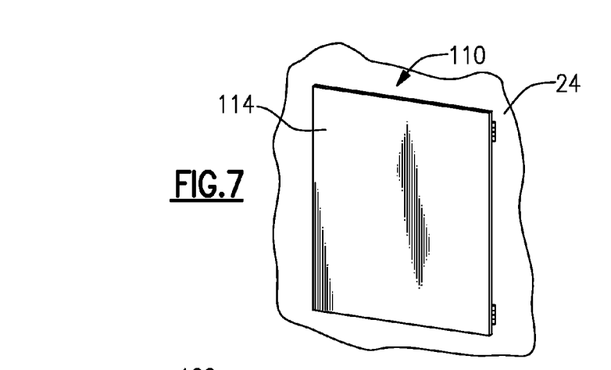
FIG. 7 is a hallway-side view of the wall-mounted pass-through dispensing cabinet of a second embodiment, here with the hallway-side door closed.

FIG. 6 is a hall-way view of the wall-mounted pass-through medications cabinet 10 mounted in the wall 24 of the patient room. Here a door 30 to the patient room is shown, as is a pharmacy cart 32 in which the pharmacy staff bring preloaded medications bins to be loaded into the respective compartments of the cabinet 10. Here the door 14 is open for pharmacy access to the bins 18 for that specific hospital room. Typically, the pharmacy staff would remove the empty bins 18 and replace them with pre-loaded bins from the pharmacy cart 32.

The bins 18 can be of the general type discussed in my earlier U.S. Pat. Nos. 7,668,620 and 6,775,591. However, the invention should not be limited to a particular style, size, or shape of bin or drawer.

Another medications cabinet 110 embodying this invention is shown in FIGS. 7 to 11. The cabinet 110 is built into a hospital wall 24 that separates the room interior from the hallway or corridor, and is positioned above the floor of the room at a height intended for convenient access by the nurse staff. The wall-side door 114 (FIG. 7) lies substantially flush against the wall on the hallway side, and swings open (FIG. 8) to reveal an access space 115 adjacent pull-out bins 118 that are stacked in a cabinet box 111. The box 111 is offset from the location of the door 114, as generally shown in broken line. At the room interior, the cabinet 110 has a room-side access door 112 (FIG. 9) positioned at the space 115 alongside the box 111. When closed, the door covers the access space 115. The door 112 swings open (FIG. 10) to open up the access space 115 to permit the nurse staff to pull out the medications bin 118 of a respective patient in the room. The bins or drawers 118 extend laterally, and lie parallel to the wall. These bins are elongated in the horizontal, lateral direction, minimizing the degree that the cabinet projects into the room interior.

Figures 8, 10:
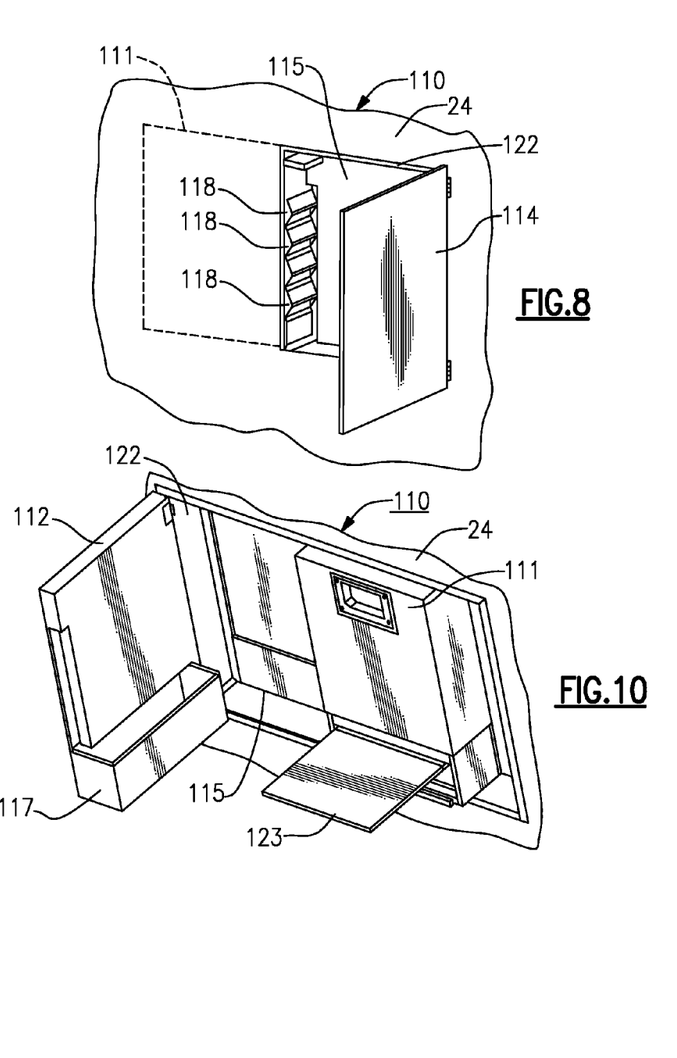
FIG. 8 is a hallway-side perspective view thereof showing the hallway-side door open, with dash line illustrating the general position of the frame of the cabinet concealed in the wall.
FIG. 9 and FIG. 10 are room-side perspective views thereof with the room-side access door closed, and with the access door open, respectively.
Figure 9:
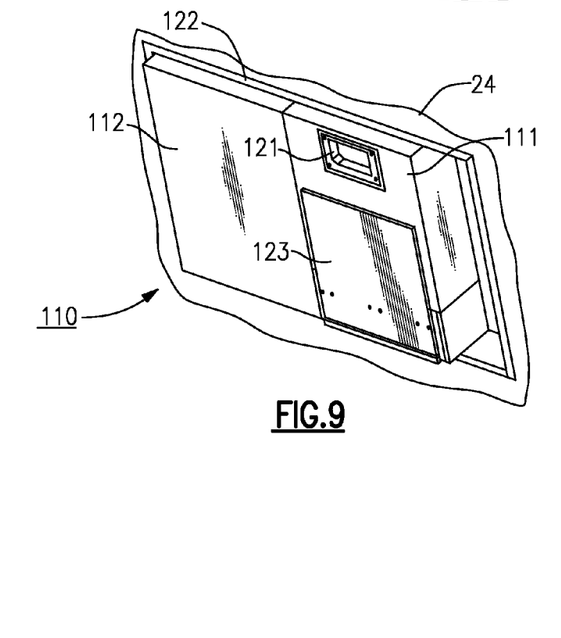

At the base of the door 112 there is a shelf 117, here in the form of a transverse box with walls and an open top, in which can be stored general medical supplies, such as bandages, wipes, gloves, disinfectants and the like. The medications box 111 and the swing-out door 112 are mounted in a frame 122 that is built into the wall 24.

Figure 11:
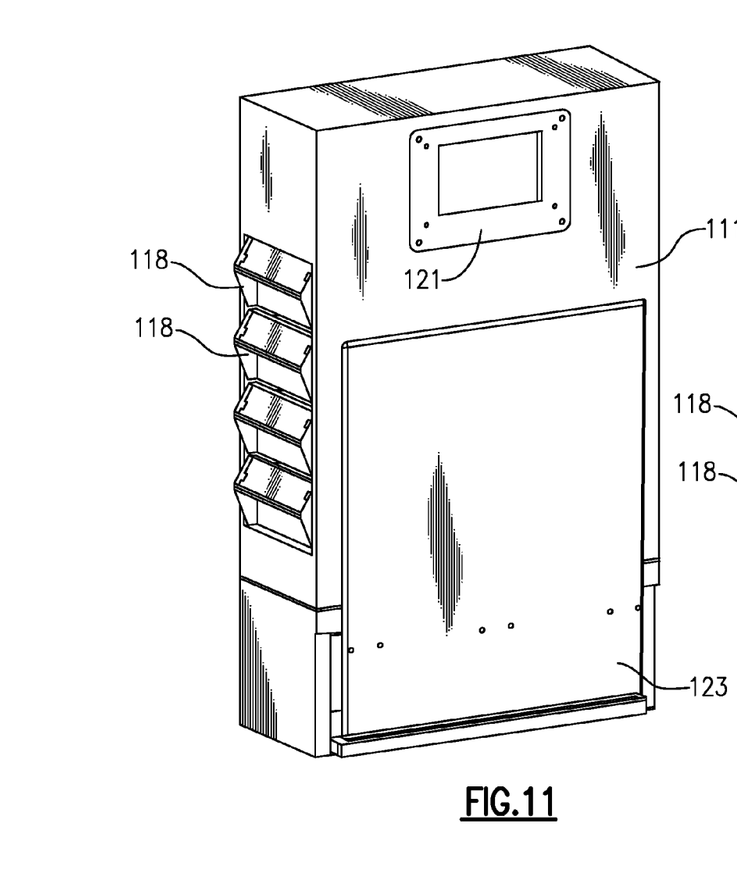
FIGS. 11 and 12 are perspective views of the cabinet box of this embodiment, here showing the tip-down support shelf in a raised position and in a lowered position, respectively.
Figure 12:
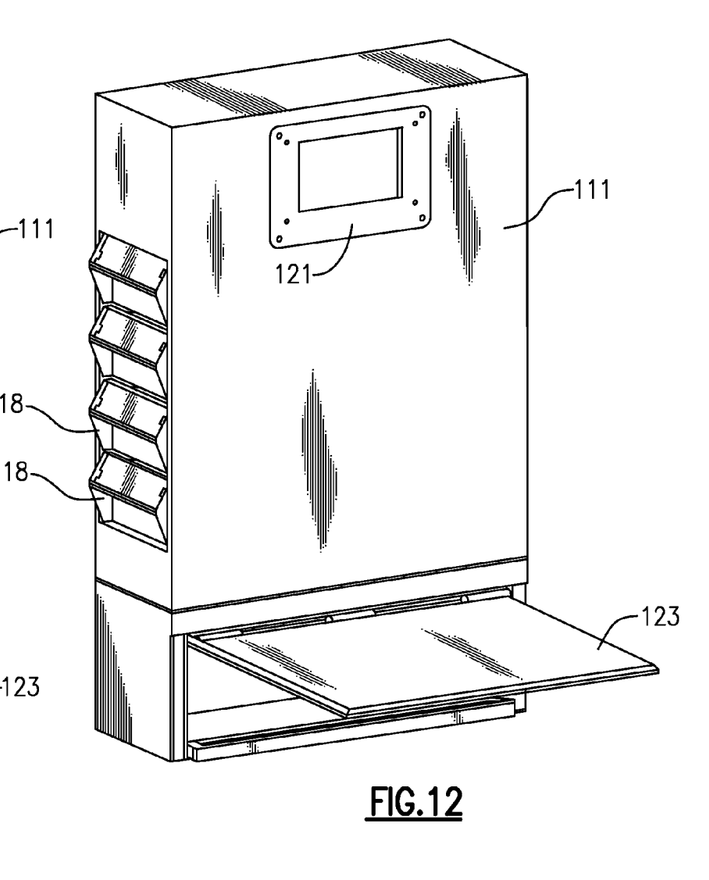

The medications box 111 holds the pull out bins 118 (four bins in this embodiment) in a vertical stack, one bin above the other, and these pull out to the left, i.e., into the space 115. The bins 118 can be accessed from the interior of the room only when the door 112 is open, and the medications box is provided with a locking mechanism such that the bins or drawers 118 can be pulled out and removed only one bin at a time. Each bin 118 must be replaced and pushed fully back in before the next bin can be removed. As shown in FIGS. 11 and 12, a touch screen device 121 is positioned at the upper part of the proximal wall of the cabinet box 111. Below that, there is a tip-down shelf 123, that pivots on a horizontal axis, and tips from a vertical storage position (FIG. 11) to a horizontal position (FIG. 12) where the shelf can be used to support a medications bin 118 for administration of the prescribed medications to the patient. The touch screen 121 can be used for obtaining access to the particular patient's bin or drawer 118 and to release a locking mechanism in the cabinet box 111. This device can also track access and attempted access, to maintain an access trail for medications and patient treatment times.

As in the first embodiment, there is an interlock so that only the hallway-side door 114 or the room-side door 112 can be opened, and preventing both doors to be opened at the same time. This feature enhances patient safety and ensures patient privacy, as it is not possible to see into the room when either the hallway-side door or the room-side door is opened.

Figure 12A:
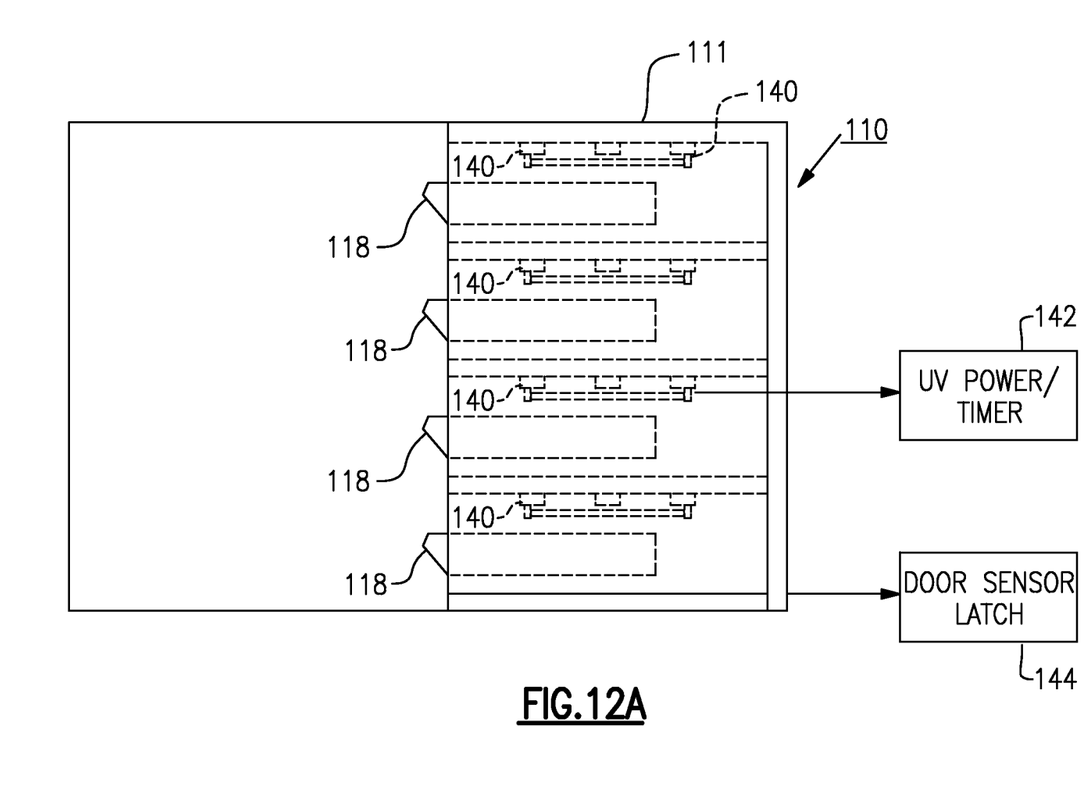
FIG. 12A is schematic elevational view for illustrating the UVGI feature incorporated into this embodiment.
Figure 13:
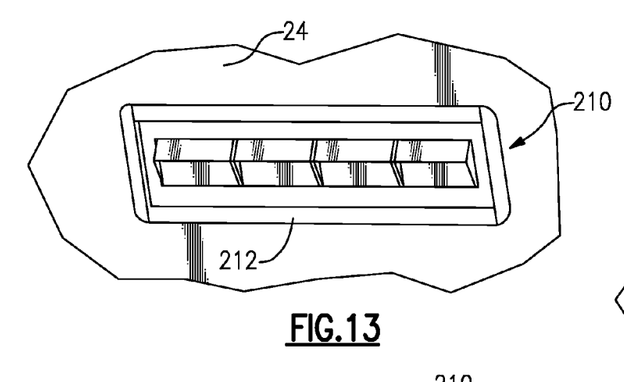
FIGS. 13 and 14 are perspective views of a pass-through medications cabinet of yet another embodiment as seen from the room side and hallway side, respectively.

As shown in FIG. 12A, in this embodiment there is an array of ultraviolet germicidal illuminator (UVGI) devices 140 disposed on within the cabinet box 11 above each of the respective pull-out bins 118. As in the first-described embodiment, these devices 140 can favorably be implemented from UV fluorescent tubes, but UV LEDs, generating UV-C radiation at a wavelength at or near about 265 nm, could be employed. An associated UV power and timer circuit 142, shown schematically, energizes these devices 140 during a sterilization cycle of a programmed duration. This circuit 142 is coupled to a drawer or bin sensor and latch control circuit 144, such that the sterilization cycle commences when the control circuit 144 senses that the bins 118 have been inserted and pushed in, and holds the latch mechanisms closed until the sterilization cycle has timed out. The UVGI devices 140 bathe the bins 118 and their contents with sufficient short wavelength UV radiation to destroy pathogens acquired from handling and transport. Other types of UV light sources could possibly be employed, so long as the UV radiation is incident on the entire contents of the cabinet, including the bins 118 and their contents.

In either of these embodiments, and in many other possible embodiments, the pass-through medications cabinet have the features of access to locked medications storage both from inside the room (for administration to the patient) and from the hallway (for the pharmacy staff), with individual locking drawers or compartments. The hallway side can be constructed to be fireproof and/or smoke-proof, so as to meet relevant building standards. There is access from only one side at a time, which maintains privacy in patient rooms. The bins or drawers can be removed from either the room side or the hallway side. The device can sense door opening and/or bin opening, and maintains an audit trail. One bin only at a time can be accessed in the room. The cabinet has electronic locking and unlocking, but also includes a manual over-ride feature for emergency use e.g. during a power failure. In room access may be by touchscreen panel, membrane switch, PC control or other system that is compatible with the hospital network. The outer or hallway-side access may employ touchscreen panel, membrane switch, RFID, or PC control, and there may be manual locking also on the hallway side, with pharmacy control of the physical key. Other beneficial features of the wall-mounted cabinet of U.S. Pat. No. 7,668, 620 can also be incorporated into this pass-through medications cabinet system.

This cabinet can be configured without a hall-side door, i.e., accessed only from within the patient room, but with the ultraviolet sterilization features which would automatically turn ON and bath the bins and their contents in UV radiation for a prescribed number of minutes once the bins are loaded into the cabinet.

A third possible preferred embodiment is illustrated in FIGS. 13 to 17, and comprises a medications cabinet 210 having a frame 222 mounted in the hospital room wall 23, as with the other embodiments so that a proximal end (FIG. 13) is presented to the inside of the hospital room and a distal or exterior end (FIGS. 14, 15) is accessible from the hallway or corridor. In this embodiment, there is a row of pull-out medication bins or drawers 18, each arranged to pull or slide out when accessed by nurse staff with proper electronic authorization. Typically the cabinet is responsive to an access device carried by authorized care staff. In this embodiment, the drawers or bins unlatch and pull out one at a time, and there is a drawer presence sensor and interlock arrangement such that each drawer or bin 218 has to be returned and pushed in before another can be accessed from inside the room. Here, the cabinet 210 is designed so that an interior face 212 of the cabinet is substantially flush with the interior surface of the wall 23, and does not project into the hospital room.

As shown in FIGS. 14 to 17, at the exterior or hallway side, the medications cabinet 210 has a hall-side closure lid or door 214, with hinges 215 at an upper side of the cabinet, so that the door lifts up or swings up for pharmacy access to the row of bins or drawers 218. There is a lock mechanism for the lid or door 214, concealed here within the frame 222, which can be unlocked to release the lid for pharmacy personnel with proper electronic access, as with the earlier-described embodiments. At the distal end of the cabinet is a bin latching mechanism 226, here shown partly concealed beneath a cover, and which interacts with cooperating latch structure 227 on each of the bins 218 (see FIG. 17). These release to permit the pharmacy staff to lift out the medication bins 218 from the hallway side, and to replace them with fresh, pre-loaded bins.

Figure 16:
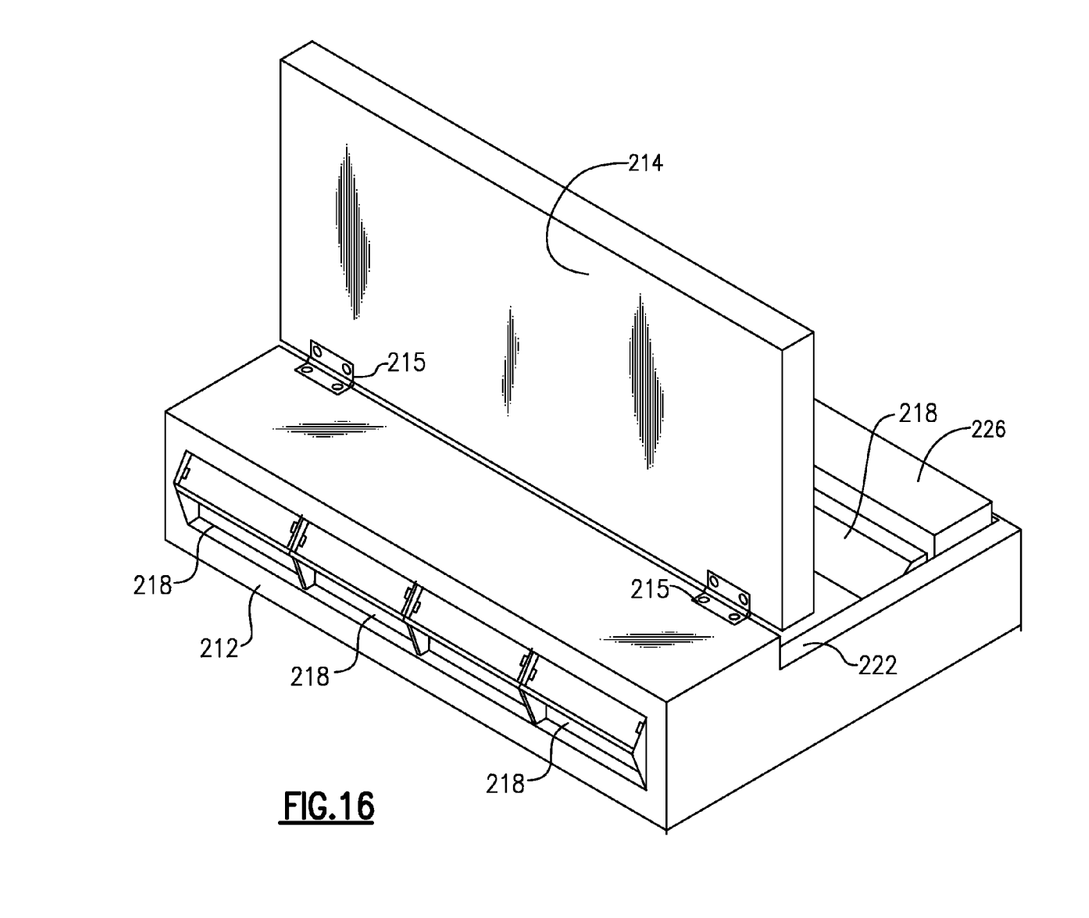
FIGS. 16 and 17 are additional perspective views of the cabinet of this embodiment.

As shown also in FIG. 16, the drawers or bins 218 each have handle or grip structure formed or molded into them at the proximal end. In some embodiments, the bins may reside in respective pull-out drawers, rather than serving as both bin and drawer.

Figure 14:
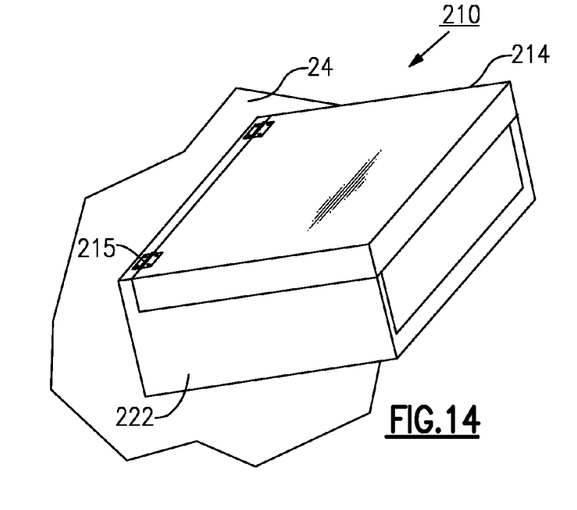
Figure 15:
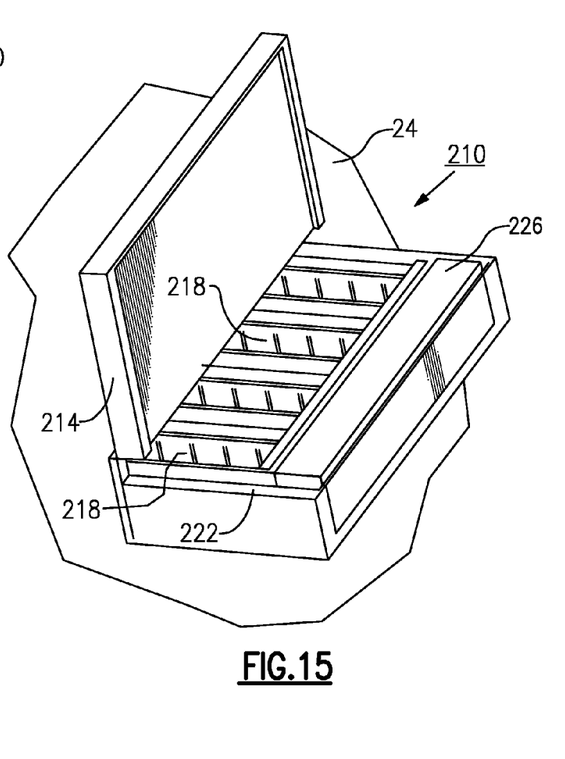
FIG. 15 is a hallway-side perspective view thereof.

In this embodiment, the cabinet distal end projects out into the hallway side of the wall 23, as shown in FIGS. 14 and 15. However, in other possible embodiments, the distal end of the cabinet could be flush with the hallway side of the wall. If desired, the cabinet frame 222 could be mounted in a slide fitting, and could be pulled out from the wall for pharmacy access to the medications bins. Also, it is possible that there could be two or more rows of bins, to satisfy a given hospital requirement. In other possible embodiments, the row of bins 218 could be disposed as a vertical row.

Figure 17:
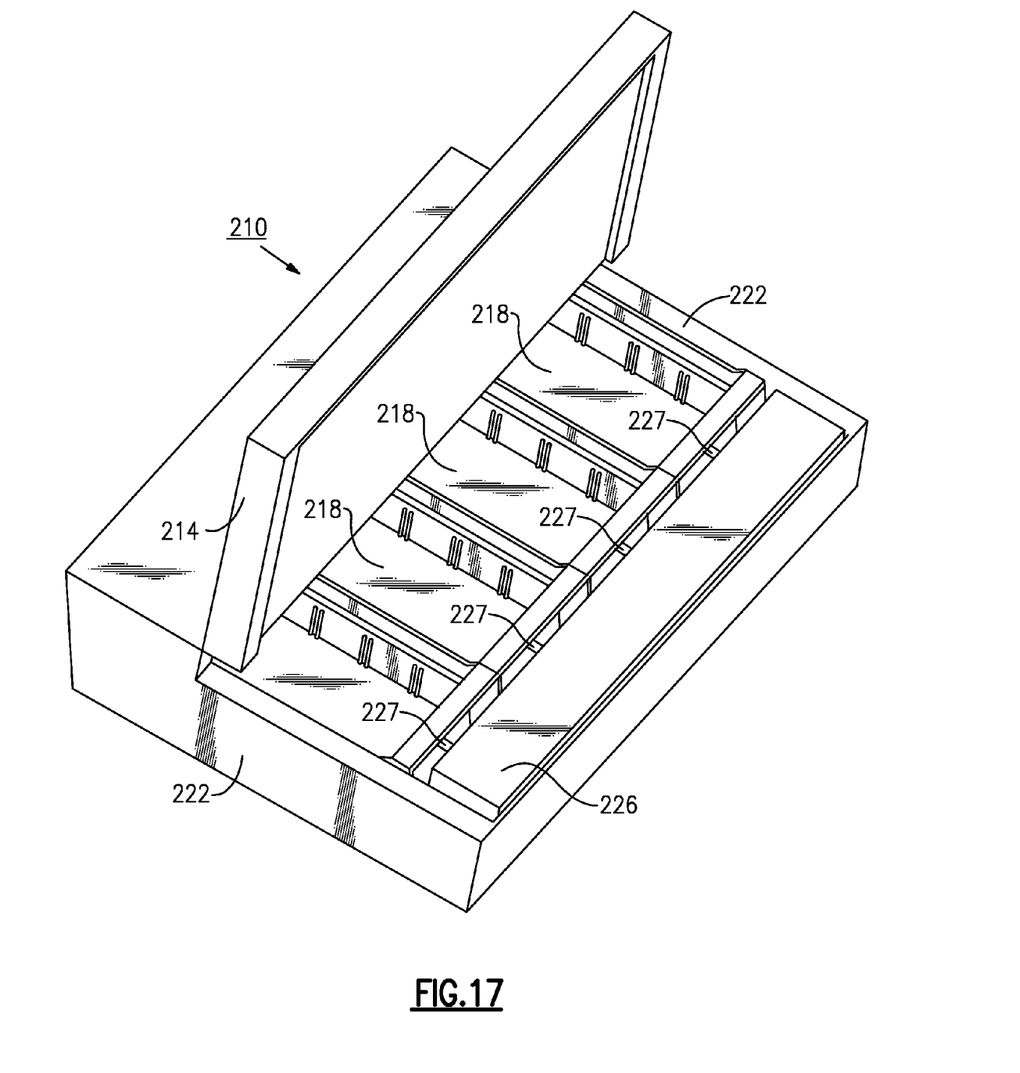
Figure 17A:
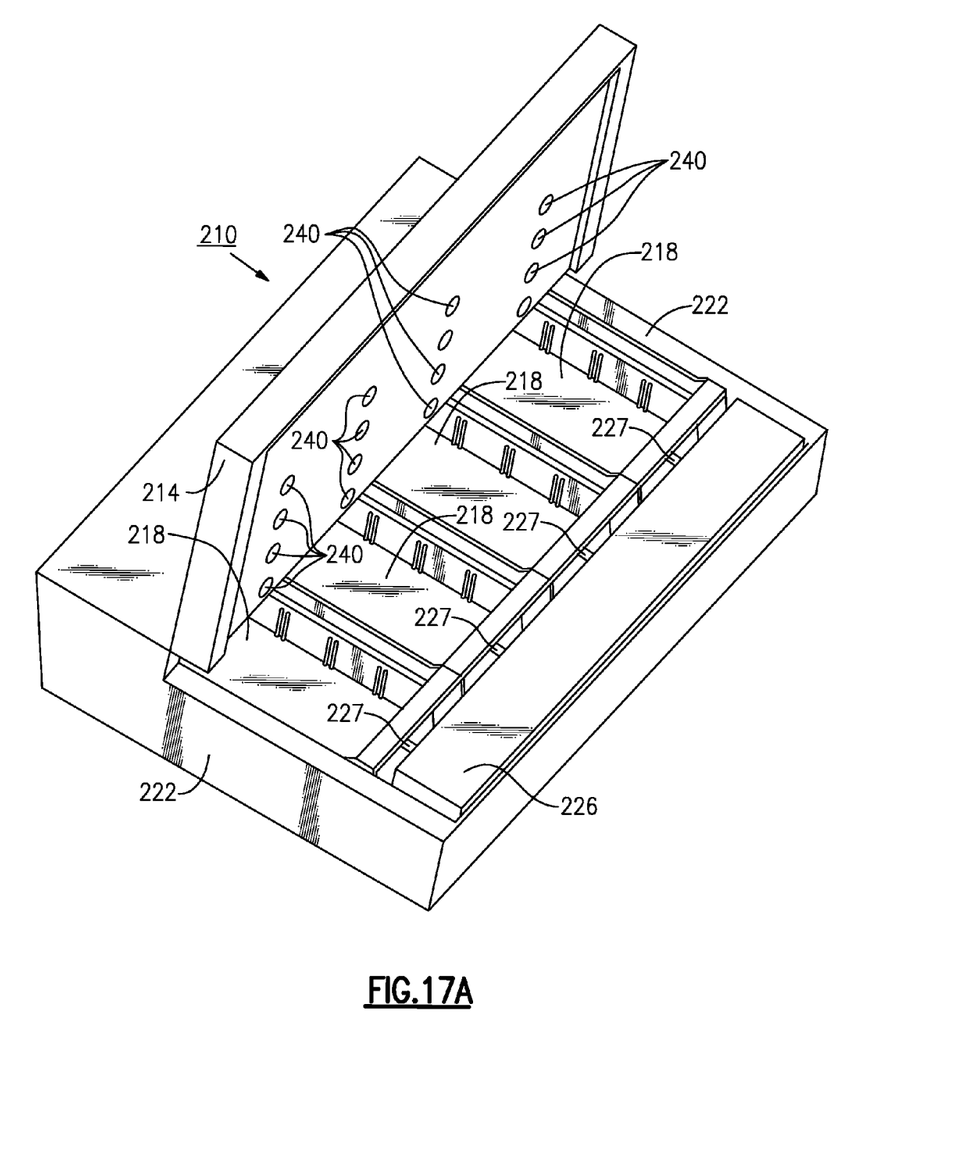
FIG. 17A is a perspective view illustrating the UVGI feature incorporated into this embodiment.

There may be one or two fluorescent tubes disposed in the lid or cover 214 to provide sterilizing UV radiation when the cover 24 is closed. A shown in FIG. 17A, the UVGI devices may be implemented as an array of UV LEDs 240 disposed in rows in the underside of the door or cover 214, such that the rows are situated above the respective bins 218. There are an associated UV power and timer circuit and door latch sensor control, as described and shown in the foregoing embodiments, but not specifically illustrated here. In this case, the UVGI devices 240 emit UV-C radiation at a wavelength at or near about 265 such that the sterilization cycle commences when the hall-side door 214 of the cabinet has been closed, and holds the latch mechanism 216 closed until the sterilization cycle has timed out. The UVGI devices bathe the bins 218 and their contents with UV radiation and destroys pathogens that may have been picked up by the bins during handling and transport.

In the arrangements described above, the UVGI feature helps stop spread of bacteria and virus from being spread patient to patient by sterilizing the pharmaceutical bins and their contents between the time of transport and the time of administration. At the same time, the control mechanisms ensure that the patients and care givers in the hospital, clinic, or other facility are protected from exposure to dangerous short wavelength radiation.

While the invention has been described in terms of selected preferred embodiments, it should be understood that the invention is not limited only to those embodiments, but rather the scope of this invention is to be measured by the appended claims.

I claim:

1. A self-sterilizing pass-through medications cabinet adapted to be mounted in a wall of a patient room, the wall separating the patient room from a hallway common to a plurality of hospital rooms; the cabinet comprising:
    an enclosure frame mounted in the wall and disposed at an elevated position above a floor of said room and having a room side that may be opened to the patient room and a hallway side that may be opened to said hallway;
    a plurality of racks supported in said frame, the racks being disposed in a stack one above another and oriented laterally in said frame;
    a plurality of medication bins disposed respectively in said racks;
    a first door located on the hallway side of the cabinet and hinged onto said enclosure frame, the first door being openable to access a plurality of said racks;
    a plurality of second doors located on the room side of said cabinet and each positioned over a respective one of said racks, each of said second doors being openable to access a medication bin in the respective rack;
    controllable door lock means associated with each of said first door and said second doors, said door lock means permitting said first door to be opened only when all of said second doors are closed, and permitting said second doors to be opened only when said first door is closed, and permitting said second doors to be opened only one door at a time;
    a plurality of ultraviolet germicidal illuminator devices disposed within the cabinet and each situated above a respective one of said medication bins; and
    associated control means sensitive to closing of said first and second doors for energizing said ultraviolet germicidal illuminator devices ON for a predetermined time when said bins have been placed in said cabinet and said doors have been closed.

2. The pass-through medications cabinet of claim 1 wherein said controllable door lock means includes an electronic latch for said first door actuable by an access device, and second door latch means for opening said second doors and actuable by a second access device, said second access device not being operative to open the electronic latch for said first door; and to hold said second doors latched closed when said germicidal illuminator devices have been energized ON until said predetermined time has expired.

3. The pass-through medications cabinet of claim 1, wherein said frame is substantially flush with said wall on the hallway side, so as not to project into said hallway.

4. The pass-through medications cabinet of claim 1, wherein said racks and said respective bins lie parallel to said wall.

5. The pass-through medications cabinet of claim 1, wherein said first door has a self-closing feature to pull said door to its closed position.

6. The pass-through medications cabinet of claim 1, wherein said first door is adapted to be smoke-proof.

7. A pass-through medications cabinet adapted to be mounted in a wall of a patient room, the wall separating the patient room from a hallway common to a plurality of patient rooms, the cabinet comprising;
    an enclosure frame mounted in the wall and disposed at an elevated position above a floor of said room and having a room side that may be opened to the patient room and a hallway side that may be opened to said hallway;
    a box mounted to one lateral side of said enclosure frame, leaving an access space within the remaining lateral side of said enclosure frame, and including a plurality of medication drawers situated one above the other in said box and disposed laterally to pull out from said box into said access space within said enclosure frame;
    a first door located on the hallway side of the cabinet and hinged onto said enclosure frame, the first door being openable to said access space within said enclosure frame;

at least one second door located on the room side of said cabinet and positioned to cover said access space and being openable from within said patient room to access said pull-out medication drawers;

controllable door lock means associated with said first and second doors, said door lock means permitting said first door to be opened only when said second door is closed and permitting said second door to be opened only when said first door is closed;

controlled access means permitting said medications drawers to be pulled out one at a time only when accessed from said room side;

a plurality of ultraviolet germicidal illuminator devices within said box and situated above each of said respective medication drawers; and control means for energizing said ultraviolet germicidal illuminator devices ON for a predetermined time period when said drawers have been pushed in to said box.

8. The pass-through medications cabinet of claim 7, wherein each of said medication drawers can be pulled out and detached from said medication cabinet box for administration of medication to a patient, and can then be re-inserted into said box and pushed back into place.

9. The pass-through medications cabinet of claim 8, wherein said box includes a swing-down shelf mounted on the room side of the box and which pivots between a raised position in which the shelf is disposed vertical and substantially flush with a proximal side of the box, and a lowered, horizontal position suitable for supporting the medications drawer during administration of said medications.

10. The pass-through medications cabinet of claim 7, wherein said second door includes a transverse shelf at a lower portion thereof adapted for storing non-medication materials.

11. The pass-through medications cabinet of claim 7, wherein said medication drawers lie parallel to said wall.

12. The pass-through medications cabinet of claim 7, wherein said first door is substantially flush with said wall on the hallway side thereof.

13. A pass-through medications cabinet adapted to be mounted in a wall of a patient room, the wall separating the patient room from a hallway common to a plurality of hospital rooms; the cabinet comprising;

an enclosure frame mounted in the wall and disposed at an elevated position above a floor of the room and having a room side that is accessible from the patient room and a hallway side that may be opened to said hallway;

a plurality of pull-out patient bins supported in respective racks in said enclosure frame, and disposed in a row oriented across said enclosure frame;

a first door located on the hallway side of the cabinet and hinged onto said enclosure frame, the first door being openable to access said racks from the hallway side;

controllable door lock means associated with said first door for locking said first door closed and permitting it to open only to an authorized access means possessed by authorized persons;

controllable drawer lock means for locking said pull-out bins to prevent access from the interior of the patient room, but permitting authorized care staff when in the interior of the room to unlock and pull out a respective one of the pull-out bins;

a plurality of ultraviolet germicidal illuminator devices situated to be above each of said respective pull-out patient bins when said first door is closed and said bins are pushed in to said racks; and control circuit means sensitive to closure said first door and said patient bins being pushed in to said racks for energizing said ultraviolet germicidal illuminator devices ON for a predetermined time period.

14. The pass-through medications cabinet of claim 13 wherein said controllable drawer lock means includes latch means for releasing said pull-out drawer, and being responsive to an access device possessed by said authorized care staff.

15. The pass-through medications cabinet of claim 14 wherein said controllable drawer lock means includes drawer sensors to detect if the pull-out bins have been pulled out or pushed in, and operative to prevent any of the medications bins to be pulled out until all the bins have been pushed back in place into the cabinet.

16. The pass-through medications cabinet of claim 13 wherein said frame is substantially flush with said wall on one of said room side and said hallway side.

17. The pass-through medications cabinet of claim 13 wherein said first door is in the form of a lid disposed horizontally and which may be lifted for access to said plurality of bins; and said ultraviolet germicidal illuminator devices include a plurality of UV LEDs arranged in rows on said lid.

18. Medication cabinet adapted to be mounted on a wall of a patient room, comprising an enclosure having a front wall and at least one side wall;

one or more locking drawers in said enclosure, each drawer including a medications bin having a proximal end disposed, when said bin is in a closed position, at said side wall and a distal end situated within said enclosure;

slide means permitting the bin to be pulled out to an open position to allow access to the bin and to be pushed back in to its closed position;

releasable latch means within said enclosure for releasably engaging a member on said bin in its closed position to lock the drawer, and being movable between a locked position and an unlocked position in which the latch means releases said member;

an ultraviolet germicidal illuminator device disposed above the respective medication bin;

automatic access means permitting an authorized person to actuate the releasable latch means to its unlocked condition to permit access to said drawer ad automatically returning said latch means to its locked position to secure the drawer bin when returned to its closed position; and control means associated with the automatic access means and with said ultraviolet germicidal illuminator devices, and sensitive to the closing of said drawers for energizing said ultraviolet germicidal illuminator devices ON for a predetermined time when said bins have been inserted into said drawers and pushed in to their closed positions.

19. The medications cabinet of claim 18, wherein said releasable latch means includes means operative to prevent the drawers from being unlocked when said ultraviolet germicidal illuminator devices have been energized ON until said predetermined time has expired.

* * * * *

UNITED STATES PATENT AND TRADEMARK OFFICE
CERTIFICATE OF CORRECTION

PATENT NO. : 8,473,097 B2  
APPLICATION NO. : 13/188102  
DATED : June 25, 2013  
INVENTOR(S) : Norman A. Shoenfeld Page 1 of 1

It is certified that error appears in the above-identified patent and that said Letters Patent is hereby corrected as shown below:

On the Title Page, item [73]

Delete "Den Argyl" should read --Pen Argyl--

Signed and Sealed this  
Sixth Day of August, 2013

Teresa Stanek Rea  
*Acting Director of the United States Patent and Trademark Office*